(12) United States Patent
Klein (10) Patent No.: US 6,174,865 B1
(45) Date of Patent: *Jan. 16, 2001

(54) METHOD OF TREATING HYPERTRIGLYCERIDEMIA WITH AN ERYTHROMYCIN COMPOUND

(76) Inventor: Ira Klein, 5 Windermere, Houston, TX (US) 77063

( * ) Notice: Under 35 U.S.C. 154(b), the term of this patent shall be extended for 0 days.

This patent is subject to a terminal disclaimer.

(21) Appl. No.: 08/937,639

(22) Filed: Sep. 25, 1997

(51) Int. Cl.$^7$ ................................. A61K 31/70
(52) U.S. Cl. ................ 514/29; 536/7.2; 536/7.4
(58) Field of Search .............. 536/7.4, 7.2; 514/29

(56) References Cited

U.S. PATENT DOCUMENTS

| | | | |
|---|---|---|---|
| 4,331,803 | 5/1982 | Watanabe et al. | 536/7.2 |
| 5,498,424 | 3/1996 | Klein | 424/464 |
| 5,786,338 | * 7/1998 | Klein | 514/29 |

OTHER PUBLICATIONS

Omura S., Structure and Stereochemistry of Macrolides, *Macrolide Antibiotics*—Chemistry, Biology and Practice, pp. 37–84 (1984).
Physicians' Desk Reference® 421–423, 425–427, 449, 651, 935, 937, 1841, and 2102 (1995).
Physicians' Desk Reference® (1995).
Physicians' Desk Reference® 405–407 (1995).
Physicians' Desk Reference® 1789–1791 (1994).
Physicians' Desk Reference® 418–426 (1994).
Physicians' Desk Reference® 1949–1950 (1993).
Schubert WK et al., Encephalopathy and Fatty Liver (Reye's Syndrome), In: *Progress in Liver Diseases,* Popper H et al. (eds.) 4th Edition, Grune and Stratton, Inc., New York, Chapter 28, pp. 489–510 (1972).
Stacher G et al., Erythromycin Effects on Gastric Emptying, Antral Motility and Plasma Motilin and Pancreatic Polypeptide Concentrations in Anorexia Nervosa, *Gut* 34:166–172 (1993).
Sturgill MG and RP Rapp, Clarithromycin: Review of a New Macrolide Antibiotic With Improved Microbiologic Spectrum and Favorable Pharmacokinetic and Adverse Effect Profiles, *Annals of Pharmacotherapy,* 26:1099–1108 (1992).
Wood MJ, The Tolerance and Toxicity of Clarithromycin, *J. Hospital Infection* 19(Supp. A):39–46 (1991).
Bryskier A. et al., Structure and Activity, In: *The New Macrolides, Azalides, and Streptogramins: Pharmacology and Clinical Applications* (Neu HC, LS Young and SH Zinner, eds.), 3:3–11 (1993).
Carlson LA and LE Bottiger, *N. Eng. J. Med.* 303(18):1061–1062 (1980).
Chaisson RE et al., Clarithromycin Therapy for Bacteremic *Mycobacterium avium* Complex Disease, *Annals of Internal Medicine* 121(12):905–911 (1994).
Flynn EH et al., Erythromycin. II. Des–N–methylerythromycin and N–Methyl–$C^{14}$–erythromycin, *J. Am. Chemical Society* 77:3104–3106 (1955).
Garg A and SM Grundy, Gemifibrozil Alone and in Combination With Lovastatin for Treatment of Hypertriglyceridemia in NIDDM, *Diabetes* 38:364–372 (1989).
Grundy SM and GL Vega, Fibric Acids: Effects on Lipids and Lipoprotein Metabolism, *Am. J. of Medicine* 83(Supp. B):9–20 (1987).
Havel RJ and E Rapaport, Management of Primary Hyperlipidemia, *New England Journal of Medicine* 332(22):1491–1498 (1995).
Kawashima A et al., New Cholesterol Biosynthesis Inhibitors MC–031 (O–Demethylchlorothricin), –032 (O–Demethylhydroxychlorothricin), –033 and 034, *Journal of Antibiotics* 45(2):207–212 (1992).
Levy RI et al., Dietary and Drug Treatment of Primary Hyperlipoproteinemia, *Annals of Internal Medicine* 77:267–294 (1972).
Merck Index, 3626, Erythromycin, 577–578 (1989).
Merck Index, 2340, Clarithromycin, 365 (1989).

* cited by examiner

*Primary Examiner*—Elli Peselev
(74) *Attorney, Agent, or Firm*—Alan H. Gordon & Associates, P.C.

(57) ABSTRACT

This invention relates to a method for treating humans having hypertriglyceridemia. Specifically, this invention provides for administration of an erythromycin compound that reduces triglyceride levels in human plasma. In particular, this invention teaches administration of clarithromycin, troleandomycin, erythromycin, and azithromycin for treating human patients with hypertriglyceridemia.

12 Claims, 2 Drawing Sheets

Figure 1

METHOD OF TREATING HYPERTRIGLYCERIDEMIA WITH AN ERYTHROMYCIN COMPOUND

BACKGROUND

1. Technical Field

This invention relates to methods and compositions for treating humans with hypertriglyceridemia using erythromycin compounds.

2. Background Information

Hypertriglyceridemia involves abnormally high concentrations of plasma triglycerides. Although an exact definition of "normal" is impossible, patients with triglyceride concentrations exceeding 150 mg/dL are generally hypertriglyceridemic. Since hypertriglyceridemia may be a risk factor for acute pancreatitis (The National Institutes of Health Consensus Development Panel, Arteriosclerosis 4:296–301 (1984) and Miller el al., Ann. Surg. 190:401–408 (1979)) as well as coronary heart disease (Carlson and Bottiger, Atherosclerosis 39:287–291 (1981)), high triglyceride concentrations require clinical attention. In most cases, non-pharmacologic treatments, such as weight reduction, dietary changes, and alcohol restriction, effectively reduce triglyceride concentrations (Levy et al., Ann. Int. Med. 77:267–294 (1972)). Other patients, however, may require drug therapy.

Pharmacologic treatment of hypertriglyceridemia involves administering drugs, such as fibric acid compounds, that influence lipid metabolism such that triglyceride plasma levels decrease. Specific fibric acid compounds in wide use today include gemfibrozil, fenofibrate, and bezafibrate. Although these drugs appear relatively safe, one major documented side effect is the development of cholesterol gallstones (Coronary Drug Project Research Group, N. Engl. J. Med. 296:1185–1190 (1977)). Further, the first fibric acid drug, clofibrate, may increase the risk of cancer (Report from Committee of Principal Investigators, Br. Heart J. 40:1068–1118 (1978)). These potential side effects, however, rarely warrant discontinued use given the triglyceride-lowering ability of fibric acid drugs as well as their tolerance by most people.

SUMMARY

The present invention relates to treating humans having hypertriglyceridemia by administering erythromycin compounds. In particular, this invention provides a method for reducing triglyceride concentrations by administering erythromycin compounds such as erythromycin, clarithromycin, azithromycin, and troleandomycin.

Using erythromycin compounds to reduce triglyceride levels is particularly beneficial because these compounds are inexpensive, easy to administer, physically tolerable, and effective. In addition, erythromycin compounds reduce low-density lipoprotein (LDL) concentrations as well as increase high-density lipoproteins (HDL) concentrations, both of which can be abnormal in hypertriglyceridemia patients (Klein, U.S. patent application Ser. No. 08/646,062). Since elevated levels of LDL and reduced levels of HDL are risk factors for severe atherosclerosis and coronary heart disease in humans (Holme et al., Arteriosclerosis 1:250–256 (1991)), using erythromycin compounds to reduce plasma triglyceride concentrations is particularly beneficial.

One aspect of this invention relates to reducing plasma triglyceride concentrations in a human by administering an erythromycin compound at doses effective to reduce plasma triglyceride concentrations. Specifically, erythromycin compounds include clarithromycin, troleandomycin, erythromycin, and azithromycin in addition to other derivatives of erythromycin. Further, these erythromycin compounds can be administered orally. Doses can range from about 100 mg/day to about 6,000 mg/day. Alternatively, doses can range from about 1 mg/kg of body weight/day to about 100 mg/kg of body weight/day, preferably from about 5 mg/kg of body weight/day to about 75 mg/kg of body weight/day, more preferably from about 10 mg/kg of body weight/day to about 25 mg/kg of body weight/day, and most preferably about 11 mg/kg of body weight/day or about 22 mg/kg of body weight/day.

Another aspect of this invention relates to treating a human having hypertriglyceridemia by administering an erythromycin compound at doses effective to reduce plasma triglyceride concentrations. Specifically, erythromycin compounds include clarithromycin, troleandomycin, erythromycin, and azithromycin in addition to other derivatives of erythromycin. Further, these erythromycin compounds can be administered orally. Doses can range from about 100 mg/day to about 6,000 mg/day. Alternatively, doses can range from about 1 mg/kg of body weight/day to about 100 mg/kg of body weight/day, preferably from about 5 mg/kg of body weight/day to about 75 mg/kg of body weight/day, more preferably from about 10 mg/kg of body weight/day to about 25 mg/kg of body weight/day, and most preferably about 11 mg/kg of body weight/day or about 22 mg/kg of body weight/day.

Another aspect of this invention relates to treating a human diagnosed with hypertriglyceridemia by administering an erythromycin compound at doses effective to reduce plasma triglyceride concentrations. Specifically, erythromycin compounds include clarithromycin, troleandomycin, erythromycin, and azithromycin in addition to other derivatives of erythromycin. Further, these erythromycin compounds can be administered orally. Doses can range from about 100 mg/day to about 6,000 mg/day. Alternatively, doses can range from about 1 mg/kg of body weight/day to about 100 mg/kg of body weight/day, preferably from about 5 mg/kg of body weight/day to about 75 mg/kg of body weight/day, more preferably from about 10 mg/kg of body weight/day to about 25 mg/kg of body weight/day, and most preferably about 11 mg/kg of body weight/day or about 22 mg/kg of body weight/day.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DETAILED DESCRIPTION

The invention involves methods for treating a human having hypertriglyceridemia. Specifically, humans having triglyceride concentrations exceeding 150 mg/dL can receive oral doses of erythromycin compounds ranging from about 100 mg/day to about 6,000 mg/day or, alternatively, from about 1 mg/kg of body weight/day to about 100 mg/kg of body weight/day.

Pharmaceutical compositions of erythromycin compounds can be formulated so that the compositions are suitable for oral administration. For example, capsules or tablets can contain erythromycin compounds in enteric form. The quantity of effective dose supplied by each capsule or tablet is relatively unimportant since total dosage can be reached by administrating either one or multiple capsules or tablets or both. Capsules may contain any well known pharmaceutically acceptable material such as gelatin and cellulose derivatives and tablet formulation can follow conventional procedures that employ solid carriers, lubricants, and the like. For example, solid carriers can be starch, sugar, or bentonite.

In addition to oral administration, erythromycin compounds can be administered intravenously, intramuscularly, intraperitoneally, topically, or the like since the route of administration as well as dose can depend on a variety of factors, such as treatment environment, patient compliance, patient tolerance, and therapeutic goals. Further, erythromycin compounds may be administered on a continuous or an intermittent basis.

Erythromycin compounds belong to the general class of antibiotics known as "macrolides" (Bryskier et al., Structure and activity in: The new macrolides, azalides, and streptogramins: Pharmacology and clinical applications, 3:3–11 [Neu, H. C., Young, L. S., and Zinner, S. H., eds.] (1993) and Omura, Macrolide Antibiotics—Chemistry, Biology and Practice (1984)). Macrolide antibiotics are lipophilic molecules having a characteristic central lactone ring bearing 12 to 17 atoms, fewer than 5 but typically no double bonds, typically no nitrogen atoms, and several amino and/or neutral sugars attached to the lactone ring. One group of somewhat atypical macrolide antibiotics is lankacidin derivatives, 17 membered-ring macrocyclic antibiotics that do not have sugars attached to the aglycone ring. Another group of somewhat atypical macrolide antibiotics is azalide compounds that contain an endocyclic nitrogen, namely azalide, within the aglycone ring.

Examples of macrolide antibiotics include synthetic, semi-synthetic, and naturally occurring compounds such as methymycin, neomethymycin, YC-17, litorin, erythromycinA to F, oleandomycin, roxithromycin, dirithromycin, flurithromycin, clarithromycin, davercin, azithromycin, troleandomycin, josamycin, kitasamycin, spiramycin, midecamycin, rokitamycin, miokamycin, lankacidin, and derivatives of these compounds. Erythromycin compounds as used herein include erythromycin and erythromycin derivatives such as clarithromycin, azithromycin, and roxithromycin. For purposes of this disclosure, erythromycin compounds also include functionally related compounds such as troleandomycin.

A strain of *Streptomyces erythrueus* produces erythromycin, which is a basic compound that readily forms salts with acids. Erythromycin has a chemical formula of $C_{37}H_{67}NO_{13}$ and a molecular weight of 733.92 (see Physicians' Desk Reference®, 421–423, 425–427, 449, 651, 935, 937, 1841, and 2102, (1995)). Erythromycin can also include but is not limited to erythromycin ethylsuccinate, erythromycin estolate, erythromycin stearate, and erythromycin lactobionate. Abbott Laboratories, Boots Pharmaceuticals, Parke-Davis, Dista Products Company, Ross Laboratories, and Pfizer Roerig distribute erythromycin under a variety of trademark names such as Erythromycin Delayed-Released Capsules (USP)™, E-Mycin™, ERYC™, Ilotycin™, Pediazole™, and TAO™.

Clarithromycin is also known as 6-0-methylerythromycin and has a chemical formula of $C_{38}H_{69}NO_{13}$ and a molecular weight of 747.96 (see Physicians' Desk Reference®, 405–407, (1994)). Clarithromycin is commercially available from Abbott Laboratories under the trademark Biaxin™ and described with other related erythromycin compounds (Watanabe et al., U.S. Pat. No. 4,331,803). Thus, clarithromycin and Biaxin™ have the same meaning and can be used interchangeably.

As a dihydrate, azithromycin is a white crystalline powder with a chemical formula of $C_{38}H_{72}N_2O_{12}2H_{20}$ and a molecular weight of 785.0 (see Physicians' Desk Reference®, 1789–91, (1994)). Azithromycin differs from erythromycin in that a methyl substituted nitrogen atom is incorporated into the lactone ring. Pfizer Laboratories Division distributes azithromycin under the trademark ZITHROMAX™.

Troleandomycin has a chemical formula of $C_{41}H_{67}NO_{15}$ and a molecular weight of 814 (see Physicians' Desk Reference®, 2102, (1995)). Troleandomycin is commercially available from Pfizer Roerig Division under the trademark TAO™.

EXAMPLES

The following examples illustrate selected modes for carrying out the claimed invention and are not to be construed as limiting the specification and claims in any way. These examples are provided so as to enable those of ordinary skill in the art to make and use the invention. These examples are not intended to limit the scope of what the inventor regards as the invention. Efforts have been made to ensure accuracy with respect to numbers used to characterize the conditions; however, some experimental errors and deviations may be present.

Example 1
Normal Levels of Human Plasma Constituents

One aspect of the present invention is a method of treating hypertriglyceridemia that includes administering a dose of an erythromycin compound to a human with clinically diagnosed hypertriglyceridemia. Patients diagnosed as hypertriglyceridemic have plasma triglyceride levels greater than the "normal" range. "Normal" triglyceride levels are usually less than 150 mg/dL, however, some clinical laboratories have recently changed that to less than 200 mg/dL. For purposes of this invention, patients having plasma triglyceride concentrations greater than 150 mg/dL were considered hypertriglyceridemic. Table 1 contains a list of basic plasma components and their "normal" plasma concentrations as reported from a typical clinical laboratory. These values aid physicians in diagnosing and monitoring patients.

TABLE 1

Normal levels of human plasma components

| Basic Components | "Normal" Plasma Concentration |
|---|---|
| Glucose | 60–110 mg/dL |
| Uric Acid | 1.9–6.8 mg/dL |
| BUN | 8–22 mg/dL |
| Creatinine | 0.5–1.7 mg/dL |
| Sodium | 135–145 mEq/L |
| Potassium | 3.5–5.3 mEq/L |
| Chloride | 94–108 mEq/L |
| Calcium | 8.5–10.7 mg/dL |
| Phosphorus Inorganic | 2.5–4.6 mg/dL |
| Total Protein | 6.4–8.4 g/dL |
| Albumin | 3.0–5.5 g/dL |
| Globulin | 1.9–4.0 g/dL |
| A/G Ratio | 1.1–2.3 |
| Total Bilirubin | 0.2–1.3 mg/dL |
| Alkaline Phosph atase | <136 U/L |
| SGOT (AST) | <49 U/L |
| SGPT | <54 U/L |
| GGT | <33 U/L |
| LD (LDH) | <231 U/L |
| Iron | 40–180 µg/dL |
| Triglycerides | <200 mg/dL |
| Total Cholesterol | 120–199 mg/dL |
| HDL Cholesterol | >35 mg/dL |
| LDL Cholesterol | <130 mg/dL |
| Total Chol/HDL Ratio | <4.5 |
| LDL/HDL Ratio | <3.3 |
| White Blood Count | 3.9–11.3 K/uL |
| Red Blood Count (RBC) | 3.8–5.1 M/uL |
| Hemoglobulin (Hgb) | 11.6–15.4 gm/dL |
| Hct | 34.0–46.0% |
| MCV | 80–98 fL |
| MCH | 27–34 pg |
| MCHC | 32–36 gm/dL |
| RDW | 11.0–15.5 |
| MPV | 7.5–11.5 fL |
| Platelets | 150–400 K/uL |
| Neutrophils | 38.0–80.0% |
| Lymphocytes | 15.0–49.0% |

Example 2
Therapeutic Administration of an Erythromycin Compound

A patient in need of treatment for hypertriglyceridemia was identified by measuring plasma triglyceride concentrations. Patients with triglyceride levels exceeding 150 mg/dL were considered hypertriglyceridemic. In most of these cases, patients were also analyzed for hypercholesterolemia by measuring cholesterol levels or by other standard diagnostic techniques such as evaluating family history of hypercholesterolemia and patient history of atherosclerosis. Hypercholesterolemia was defined as a total cholesterol level greater than 200 mg/dL, an HDL cholesterol level less than 35 mg/dL, an LDL cholesterol level greater than 130 mg/dL, a total cholesterol to HDL cholesterol ratio greater than 5.1, or a LDL cholesterol to HDL cholesterol ratio greater than 3.7. To determine baseline levels of plasma triglycerides as well as total cholesterol, HDL cholesterol, and LDL cholesterol, five milliliters of blood were drawn from patients and analyzed using standard laboratory procedures available to physicians.

Following patient identification, a complete medical history was obtained with emphasis on potential adverse reactions to or contraindications for the use of erythromycin compounds. The desired reduction of triglyceride concentration was then determined based on a comparison of the patient's present baseline plasma triglyceride level and normative values in addition to the physician's professional judgment. In most cases, the desired reduction in total plasma cholesterol, LDL cholesterol, LDL/HDL ratio, and total plasma cholesterol/HDL ratio as well as the desired elevation of HDL cholesterol was determined based on a comparison of the patient's present baseline plasma cholesterol levels and normative values in addition to the physician's professional judgment. The effective dose for treating hypertriglyceridemia and/or hypercholesterolemia, the interval between doses, and the duration of treatment were then determined on a case-by-case basis. Previous observations with regard to clarithromycin were made in part from clinical trials as reported in U.S. Pat. No. 5,498,424 and in co-pending United States Patent Applications having Ser. No. 08/658,837 and 08/646,062.

Informed consent was obtained from all patients with regard to the potential benefits and risks of the experimental protocol. Patients were informed that clarithromycin had not been approved by the United States Food and Drug Administration for treatment of hypertriglyceridemia or hypercholesterolemia. Once informed, patient consent was obtained and Biaxin™ treatment initiated.

Each patient entered into the study was followed at appropriate intervals, usually weekly, during treatment by having plasma triglyceride and cholesterol levels measured. To measure plasma components, each patient usually had a complete CBC and SMA-29 work-up. For CBC work-up, 5 milliliters of blood were drawn into a Vacutainer™ tube with 0.05 ml of 15% EDTA (K3) solution (7.5 mg). The tube had a silicone lubricated stopper, a lavender top for identification, and no interior coating. For SMA-29 work-up, 5 milliliters of blood were drawn into an empty Vacutainer™ tube with a red top for identification. The blood was then centrifuged and results obtained by examination of the serum using an automated processor. Automated processors are readily available through routine laboratory services provided to all physicians. In addition, automated processors were calibrated and routinely checked and re-calibrated, if necessary. The resulting data were then analyzed and the percent change over time calculated. Further, patient histories were updated and, if necessary, doses modified as determined by the clinician.

Other medications being taken by each patient were reviewed in detail by the clinician. Patients on certain medications or with histories of certain diseases were excluded from participation in the trial. Patients taking other cholesterol or triglyceride reducing medications were instructed to stop taking such medications for at least one week before initiating clarithromycin treatment. In addition, each patient had a physical examination. Hypertension was extremely common in this patient population. Patients on angiotensin conversion enzyme (ACE) inhibitors were transferred to an alpha blocker, prazosin, if they were diabetic; and transferred to a beta blocker, atenolol, if they were not diabetic. Beta blockers were avoided with diabetes mellitus as they may hide symptoms of hypoglycemia. Diabetes was also quite common in this population. Optimum control of diabetes was provided with either insulin or oral hypoglycemic medication.

In general, each patient received one dose of clarithromycin every 48 hours. The dose provided was about 10 mg per pound of body weight per 48 hours (22.2 mg per kilogram of body weight per 48 hours), which is equivalent to about 11 mg/kilogram of body weight/day. Because clarithromycin was available by prescription as 500 mg tablets, most patients received a single dose of 500 mg per 50 pounds of body weight on each day of treatment. The dose was modified, increased or decreased, by the physician as a result of the patient's response to treatment.

Women developed nausea more frequently with ingestion of clarithromycin than men. Thus, all women were instructed to take a 250 mg tablet of Tigan™ (See Physicians' Desk Reference®, page 2419, (1995)) upon awakening each day clarithromycin was to be taken. In addition, all women were instructed to wait 30 minutes before taking the full dose of clarithromycin. Further, the medication was to be taken with water only and not with food. Men were instructed to take the medication upon awakening without food.

Patients were informed that they might experience a bad taste as a result of the medication. Although this bad taste had a beneficial effect of reinforcing a decrease of food intake, patients were also told that additional side effects, such as abdominal cramps, nausea, and diarrhea, might occur during the first and second doses. In addition, some patients reported one or two loose bowel movements within 4 hours of taking the medication. These symptoms generally decreased thereafter with continued use. Patients were also instructed to call a physician immediately upon any suspicion of an allergic reaction such as hives, skin rash, or breathing difficulty. In addition, any persistent diarrhea, fever, or rectal bleeding was to be evaluated as soon as possible. Importantly, the medication was discontinued if any significant abnormalities on the blood tests arose. In particular, the physician monitored each patient for indications of hepatic or renal dysfunction as well as a reduction in white blood cell or platelet count as these can indicate rare side effects of the medication.

Since weight control was critical to maintaining normal triglyceride and/or cholesterol levels, all patients were advised about eating habits and food intake. Regarding dietary instructions, patients were advised to avoid ingestion of bread, potatoes, deserts, snacks, and foods labeled low cholesterol or low fat. With most patients, simplicity of instructions was important. Evaluating each patient's weight, blood pressure, and blood tests during a weekly check-up allowed the physician to reinforce the importance of diet to help improve health. During discussions about dieting, patients were also provided with basic information regarding the mechanism behind successful weight loss and maintenance of weight loss.

Once normal plasma levels of triglyceride and/or cholesterol were established and an ideal body weight achieved, clarithromycin was discontinued. Some patients, however, continued on the medication as prophylactic therapy. Since the maintenance of normal triglyceride and/or cholesterol levels and ideal body weight without medication varies, triglyceride and/or cholesterol levels were monitored closely after cessation of medication to determine if further treatment was necessary.

Effects of clarithromycin on weight, cholesterol levels, and triglyceride levels for each patient are presented as a percent change from the onset of treatment (Tables 2–9). Each table contains data collected for a given month after initial treatment. For example, the data presented in Table 2 were collected from patients in the first month of treatment. Since measurements were made weekly, the patient value for each month represents averages from up to four independent measurements. For convenience, patients diagnosed with hypertriglyceridemia are presented in bold type and marked with an asterisk.

TABLE 2

Effect of clarithromycin on weight, cholesterol levels, and triglyceride levels after one month of treatment.

| Patient # | Weight | Total Cholesterol | HDL | LDL | Total Cholesterol/HDL | LDL/HDL | Triglycerides |
|---|---|---|---|---|---|---|---|
| 1001 |  | −15.4 | 30.6 | −26.1 | −34.4 | −43.5 |  |
| 1002 |  | −13.3 | −20 5 | −16.9 | 9.6 | 4.3 |  |
| 1003 | −1.1 | 8.6 | −10.2 | 14.0 | 20.4 | 26.3 |  |
| *1004 | −3.6 | −29.1 | −12.2 | −30.2 | −19.2 | −19.6 | −37.2 |
| 1005 | 4.5 | −11.3 | 9.7 | −10.2 | −15.4 | −18.4 |  |
| 1006 | −4.0 | −22.6 | 28.6 | −23.0 | −35.5 | 40.8 |  |
| *1007 | −5.7 | 2.2 | 18.5 | 25.7 | −15.3 | −1.9 | −56.4 |
| 1008 | −1.7 | −2.1 | 24.1 | −11.5 | −28.6 | −28.6 |  |
| 1009 | −5.7 |  |  |  |  |  |  |
| 1010 | −7.7 |  |  |  |  |  |  |
| 1011 | −3.9 | −16.2 | −3.1 | 13.3 | −13.5 | −11.1 |  |
| 1012 | −4.6 | 5.9 | 17.1 | 24.8 | −9.5 | 5.4 |  |
| 1013 | −7.5 |  |  |  |  |  |  |
| 1015 | −1.6 | −11.0 | 9.1 | −5.7 | −18.7 | −12.5 |  |
| *1016 | −2.6 | −20.2 | −14.0 | 2.6 | 17.4 | 37.5 | −52.6 |
| 1017 | −3.8 | −4.2 | 8.1 | 2.2 | −12.1 | −2.8 |  |
| 1018 | −3.6 | −7.0 | −5.8 | −8.0 | −2.4 | 0.0 |  |
| 1021 | −2.5 | 14.7 | 8.2 | 16.7 | 6.4 | 5.9 |  |
| 1023 | 5.5 | −8.6 | −17.2 | −8.9 | 10.2 | 10.9 |  |
| 1024 | −6.7 | −11.1 | −11.8 | −6.4 | 2.4 | 3.6 |  |
| *1025 | −2.4 | −10.9 | 29.0 | −4.1 | −30.9 | −25.8 | −43.3 |
| 1026 | −4.2 | 2.4 | −5.7 | 5.9 | 8.5 | 11.4 |  |
| 1027 | −5.5 |  |  |  |  |  |  |
| 1028 | −2.9 | −9.3 | −15.2 |  | 6.7 |  |  |
| *1029 | 3.7 | −18.9 | 117.6 |  | −63.4 |  | −63.1 |
| 1030 | −1.6 | −16.9 | −12.5 | −15.7 | −5.4 | −4.2 |  |
| 1031 | −4.5 |  |  |  |  |  |  |
| 1032 | −1.2 | −5.4 | −4.1 | 0.6 | −1.9 | 6.1 |  |
| 1033 | −1.2 | 1.4 | −20.0 | 3.8 | 25.6 | 29.2 |  |
| 1034 | −6.1 | −12.3 | −24.1 | −5.4 | 16.7 | 17.8 |  |
| 1035 | −1.8 |  |  |  |  |  |  |
| 1037 | −0.7 | −16.7 | −13.0 | −12.8 | −5.4 | 0.0 |  |

TABLE 2-continued

Effect of clarithromycin on weight, cholesterol levels, and triglyceride levels after one month of treatment.

| Patient # | Weight | Total Cholesterol | HDL | LDL | Total Cholesterol/HDL | LDL/HDL | Triglycerides |
|---|---|---|---|---|---|---|---|
| *1039 | -3.6 | -15.9 | 17.1 |  | -27.8 |  | -20.0 |
| 1040 | -1.4 | -32.4 | -16.7 | 4.9 | -19.7 | 8.8 |  |
| *1042 | -4.9 | 6.4 | 6.5 | 20.3 | 0.0 | 12.7 | -3.6 |
| *1043 | -2.9 | 5.6 | -5.0 | 9.9 | 10.4 | 15.8 | 1.9 |
| 1044 | -3.5 |  |  |  |  |  |  |
| *1045 | -6.2 | -11.2 | -7.5 | -9.7 | -3.6 | -2.8 | -19.7 |
| 1046 | -2.9 |  |  |  |  |  |  |
| 1047 | -2.4 |  |  |  |  |  |  |
| 1048 | -6.2 | 0.0 | 38.7 | 11.6 | -26.9 | -20.6 |  |
| 1049 |  | 0.0 | 16.1 | -20.2 | -12.5 | -31.0 |  |
| 1051 | -4.6 | -2.5 | 6.4 | -27.7 | -23.1 | -28.1 |  |
| *1054 | -0.5 | -3.4 | -4.2 | 7.2 | -6.8 | 3.7 | -54.0 |
| 1056 | -2.1 | -1.3 | -14.7 | 18.3 | 17.1 | 35.7 |  |
| 1057 | 4.3 |  |  |  |  |  |  |
| 1058 | -4.6 | -12.8 | -16.4 | -15.2 | 4.4 | 3.6 |  |
| *1059 | -5.9 | -6.5 | -16.7 | 9.3 | 11.8 | 31.0 | -41.0 |
| 1061 | -3.8 | -6.3 | -5.6 | -17.3 | -1.4 | -11.9 |  |
| *1062 | -2.6 |  |  |  |  |  | -50.4 |
| 1063 | -5.0 | -9.6 | 2.2 | -9.5 | -12.9 | -11.1 |  |
| 1064 | -2.5 | -7.2 | -5.7 | -82 | -2.7 | -3.8 |  |
| 1065 | -3.5 | -9.4 | 15.0 | -18.4 | -21.3 | -28.3 |  |
| 1066 | -1.2 | -15.0 | -6.8 | -27.5 | -13.8 | -18.8 |  |
| 1067 | -4.8 |  |  |  |  |  |  |
| 1068 | -1.5 |  |  |  |  |  |  |
| *1069 | -5.4 | 3.9 | 3.8 | 25.0 | 0.0 | -19.6 | -35.7 |
| 1070 | -3.8 |  |  |  |  |  |  |
| *1071 | -7.5 | 9.0 | 38.0 | 21.9 | -21.0 | -10.8 | -36.4 |
| 1073 | -4.1 |  |  |  |  |  |  |
| *1074 | -1.3 | -16.7 | -16.4 | -13.3 | 2.3 | 3.8 | -24.0 |
| 1075 | -1.2 | -28.1 | -23.5 | -30.8 | -6.1 | -9.5 |  |
| 1076 | -2.4 | -26.8 | -10.5 | -31.6 | -18.9 | -22.2 |  |
| *1077 | -2.4 | -7.6 | -10.0 | 3.2 | 2.5 | 14.3 | -29.5 |
| 1078 | -2.8 |  |  |  |  |  |  |
| 1079 | -3.6 | -7.3 | 4.2 | -12.5 | -11.1 | -14.3 |  |
| *1080 | -1.9 | -5.1 | 0.0 | -4.7 | -4.3 | -3.2 | -75.1 |
| 1081 | -3.3 | -11.0 | 20.0 | -14.2 | -26.0 | -33.0 |  |
| 1082 | -5.6 |  |  |  |  |  |  |
| *1083 | -4.7 | -7.3 | 11.5 | -6.5 | -17.1 | -16.0 | -46.4 |
| 1086 | -4.6 | -18.0 | -23.1 | -29.1 | 5.4 | -7.5 |  |

TABLE 3

Effect of clarithromycin on weight, cholesterol levels, and triglyceride levels after two months of treatment.

| Patient # | Weight | Total Cholesterol | HDL | LDL | Total Cholesterol/HDL | LDL/HDL | Triglycerides |
|---|---|---|---|---|---|---|---|
| 1001 |  | -10.0 | 33.3 | -15.8 | -33.0 | -37.0 |  |
| 1002 |  | -16.8 | 10.3 |  | -24.7 |  |  |
| 1003 | -2.5 | -18.0 | 2.3 | -23.2 | -20.4 | -23.7 |  |
| *1004 | -4.0 | -18.4 | 10.2 | -17.9 | -26.0 | -25.5 | -47.2 |
| *1007 | -8.3 | -4.8 | 11.1 | 19.3 | -6.5 | 7.7 | -30.1 |
| 1008 | -2.6 | -1.7 | 41.4 | -16.9 | -30.9 | -41.3 |  |
| 1009 | -6.4 |  |  |  |  |  |  |
| 1010 | -9.4 |  |  |  |  |  |  |
| 1011 | -3.3 | -12.7 | -3.1 | -13.3 | -13.5 | -11.1 |  |
| 1013 | -8.5 |  |  |  |  |  |  |
| *1016 | -3.7 | -24.6 | -20.0 | -15.4 | -4.3 | 4.2 | -45.3 |
| 1018 | -6.5 | -7.2 | -3.9 | -10.0 | -2.4 | -3.4 |  |
| *1025 | -4.5 | -11.8 | 35.5 | -1.6 | -34.0 | -27.4 | -55.2 |
| 1026 | -6.1 | -3.6 | -7.5 | -2.2 | 4.3 | 5.7 |  |
| 1028 | -3.7 | -8.1 | -9.1 |  | -1.3 |  |  |
| *1029 | -3.3 | -9.1 | 153.0 |  | -64.6 |  | -51.2 |
| 1030 | -10.9 | -18.8 | -3.6 | -20.9 | -16.2 | -16.7 |  |
| 1031 | -7.0 |  |  |  |  |  |  |
| 1032 | 2.6 | 4.2 | 10.2 | 13.0 | -5.7 | 3.0 |  |
| 1034 | -6.5 | -3.2 | 13.0 | -2.7 | -1.4 | -14.3 |  |
| 1035 | -2.4 |  |  |  |  |  |  |
| 1037 | -3.6 | -13.4 | -18.8 | -7.7 | 5.4 | 13.0 |  |
| *1039 | -6.0 | -4.4 | 5.7 |  | -9.7 |  | -38.6 |
| *1042 | -6.4 | 8.3 | 3.2 | 23.4 | 4.5 | 16.3 | -31.6 |

TABLE 3-continued

Effect of clarithromycin on weight, cholesterol levels, and triglyceride levels after two months of treatment.

| Patient # | Weight | Total Cholesterol | HDL | LDL | Total Cholesterol/HDL | LDL/HDL | Triglycerides |
|---|---|---|---|---|---|---|---|
| *1043 | −3.9 | 7.5 | −17.5 | 17.2 | 29.9 | 42.1 | 1.1 |
| 1044 | −6.6 | | | | | | |
| *1045 | −10.0 | −16.5 | −2.5 | −15.9 | −14.3 | −11.1 | −38.3 |
| 1047 | −3.6 | | | | | | |
| 1048 | −7.0 | −5.3 | 35.4 | 0.0 | −29.9 | −25.6 | |
| 1049 | | 20.0 | 32.3 | 9.3 | −8.9 | −16.7 | |
| 1056 | −2.8 | −6.7 | −7.3 | −11.8 | 0.0 | −7.1 | |
| 1057 | −4.9 | | | | | | |
| 1058 | −5.2 | −18.1 | −7.5 | −26.7 | −11.6 | −17.2 | |
| *1059 | −5.9 | −13.1 | −19.4 | −1.3 | 7.3 | 21.4 | −39.3 |
| 1061 | −4.4 | −10.6 | −2.8 | −24.0 | −8.5 | −21.4 | |
| 1063 | −5.8 | 2.9 | 6.7 | 3.2 | −3.2 | −5.6 | |
| 1065 | −2.2 | −15.5 | 10.0 | −25.9 | −23.0 | −32.6 | |
| 1067 | −5.9 | | | | | | |
| 1068 | −7.6 | | | | | | |
| *1071 | −12.5 | −6.2 | 38.0 | 3.6 | −32.0 | −24.6 | −50.6 |
| 1072 | −3.9 | −4.6 | 8.6 | −12.6 | | | |
| *1074 | −2.2 | −16.7 | −21.3 | −12.0 | 7.0 | −11.5 | −26.7 |
| 1075 | −1.7 | −20.1 | −17.6 | −19.5 | −3.0 | −4.8 | |
| *1077 | −5.7 | −10.5 | −5.0 | 8.1 | −7.5 | 14.3 | −59.0 |
| 1078 | −5.4 | | | | | | |
| 1079 | −7.7 | −7.3 | 5.6 | −8.3 | −11.1 | −14.3 | |
| *1080 | −3.1 | −10.2 | 0.0 | −24.2 | −10.6 | −22.6 | −85.0 |
| 1081 | −6.6 | −8.8 | 26.7 | −14.8 | −28.0 | −33.0 | |
| 1086 | −3.2 | −5.5 | −21.2 | −12.6 | 19.6 | 10.0 | |

TABLE 4

Effect of clarithromycin on weight, cholesterol levels, and triglyceride levels after three months of treatment.

| Patient # | Weight | Total Cholesterol | HDL | LDL | Total Cholesterol/HDL | LDL/HDL | Triglycerides |
|---|---|---|---|---|---|---|---|
| 1007 | −6.7 | 2.6 | 7.4 | 17.1 | −4.7 | 7.7 | |
| 1010 | −9.4 | | | | | | |
| 1016 | −4.1 | −8.6 | −14.0 | −6.8 | 6.5 | 4.2 | |
| 1018 | −6.5 | −4.8 | 27.4 | −16.6 | −24.4 | −34.5 | |
| *1025 | −5.0 | −5.6 | 51.6 | 4.9 | −37.1 | −30.6 | −55.4 |
| 1026 | −9.0 | 1.2 | −1.9 | −2.7 | −4.3 | −5.7 | |
| *1029 | −3.9 | −3.0 | 158.8 | | −62.8 | | −58.2 |
| 1030 | −13.9 | −15.5 | −8.9 | −18.5 | −13.5 | −16.7 | |
| 1031 | −11.6 | | | | | | |
| 1032 | −3.7 | 4.6 | 4.1 | 8.0 | 0.0 | 3.0 | |
| 1034 | −9.3 | −11.9 | −5.6 | −12.1 | −7.1 | −7.1 | |
| 1037 | −8.3 | 0.0 | −10.1 | 7.7 | 10.8 | 17.4 | |
| 1038 | −3.7 | −2.4 | 25.8 | 7.1 | −22.9 | −15.4 | |
| *1039 | −8.9 | −24.2 | −11.4 | | −13.9 | | −64.8 |
| *1042 | −7.8 | −3.9 | 3.2 | −1.6 | −7.6 | −4.9 | −16.0 |
| 1044 | −7.7 | | | | | | |
| *1045 | −11.4 | −20.5 | 0.0 | −22.1 | −16.1 | −16.7 | −31.1 |
| 1048 | −7.5 | −5.3 | 12.9 | 11.6 | −16.4 | 0.0 | |
| 1057 | −4.3 | | | | | | |
| 1058 | −6.2 | −20.1 | 6.0 | −29.8 | −25.6 | −32.1 | |
| *1059 | −8.4 | 4.3 | −13.9 | 16.6 | 20.6 | 33.3 | −15.5 |
| 1061 | −5.1 | −5.5 | 5.6 | −12.0 | −11.3 | −16.7 | |
| *1062 | −3.0 | | | | | | −14.1 |
| 1063 | −7.6 | −3.4 | 7.8 | −3.2 | −9.7 | −11.1 | |
| 1067 | −8.2 | | | | | | |
| 1068 | −12.4 | | | | | | |
| *1071 | −10.8 | 11.4 | 52.4 | −3.6 | −27.0 | −36.9 | 34.5 |
| 1073 | −4.1 | | | | | | |
| *1074 | −1.3 | −3.0 | 0.0 | −4.4 | −2.3 | −3.8 | −1.8 |
| *1077 | −6.7 | −5.9 | −8.3 | 15.3 | 2.5 | 23.8 | −51.5 |
| 1078 | −10.1 | | | | | | |
| 1079 | −7.7 | −5.2 | 21.1 | −19.8 | −22.2 | −35.7 | |
| 1080 | −2.5 | −14.2 | −8.3 | −30.9 | −6.4 | −25.8 | |
| 1081 | −8.3 | −9.7 | 22.2 | −18.5 | −26.0 | −33.0 | |
| 1086 | −4.6 | −6.2 | −5.8 | −18.4 | −1.8 | −15.0 | |

TABLE 5

Effect of clarithromycin on weight, cholesterol levels, and triglyceride levels after four months of treatment.

| Patient # | Weight | Total Cholesterol | HDL | LDL | Total Cholesterol/HDL | LDL/HDL | Triglycerides |
|---|---|---|---|---|---|---|---|
| *1004 |  | −23.2 | −10.2 | −23.9 | −13.7 | −15.7 | −31.0 |
| 1010 | −11.2 |  |  |  |  |  |  |
| *1016 | −4.4 | −12.1 | −10.0 | 5.1 | −2.2 | 12.5 | −44.3 |
| 1026 | −11.1 | −3.6 | 7.0 | −5.9 | −10.6 | −14.3 |  |
| *1029 | −3.3 | −11.8 | 158.8 |  | −65.7 |  | −57.7 |
| 1030 | −16.9 | −3.9 | 7.1 | −2.2 | −10.8 | −8.3 |  |
| 1032 | −5.9 | 8.5 | 4.1 | 17.3 | 3.8 | 12.1 |  |
| 1034 | −12.0 | −2.2 | 1.8 | −2.9 | −4.8 | −7.1 |  |
| 1037 | −8.3 | −5.5 | −4.3 | 5.8 | −2.7 | 8.7 |  |
| *1042 | −11.3 | −16.7 | −9.7 | −11.7 | −7.6 | 22.0 | −35.1 |
| 1044 | −9.1 |  |  |  |  |  |  |
| *1045 | −10.4 | −8.9 | 5.0 | −9.0 | −12.5 | −13.9 | −22.3 |
| 1058 | −4.9 | −17.0 | 1.5 | −23.6 | −18.6 | −21.4 |  |
| *1059 | −8.4 | −10.4 | 0.0 | 7.3 | −10.3 | 7.1 | −61.7 |
| *1062 | −4.2 |  |  |  |  |  | −41.0 |
| 1063 | −8.8 | 0.4 | 6.7 | 0.0 | −6.5 | −11.1 |  |
| *1071 | −10.6 | −12.4 | 28.6 | −4.4 | −28.0 | −24.6 | −29.5 |
| *1074 | 0.0 | −8.0 | 1.6 | −13.9 | −9.3 | −15.8 | 0.9 |
| 1080 | −4.7 | −11.5 | 12.5 | −20.1 | −21.3 | −29.0 |  |
| 1081 | −10.6 | −10.6 | 22.2 | −17.9 | −26.0 | −33.0 |  |

TABLE 6

Effect of clarithromycin on weight, cholesterol levels, and triglyceride levels after five months of treatment.

| Patient # | Weight | Total Cholesterol | HDL | LDL | Total Cholesterol/HDL | LDL/HDL | Triglycerides |
|---|---|---|---|---|---|---|---|
| *1007 | −4.8 | 4.8 | 25.9 | 2.9 | −16.5 | −19.2 | −1.0 |
| 1008 | 0.0 | −7.2 | 34.5 | −26.2 | −30.9 | −44.4 |  |
| 1010 | −10.6 |  |  |  |  |  |  |
| 1018 | −8.9 | −11.0 | 3.9 | −20.7 | −14.6 | −24.1 |  |
| *1029 | −3.1 | −20.2 | 117.6 |  | −63.4 |  | −77.4 |
| 1030 | −19.1 | −16.9 | 7.1 | −21.6 | −21.6 | −25.0 |  |
| 1037 | −8.3 | 6.0 | 8.7 | 8.3 | −5.4 | 0.0 |  |
| *1042 | −10.8 | −0.5 | 41.9 | 10.9 | −30.3 | −22.0 | −61.3 |
| 1044 | −7.7 |  |  |  |  |  |  |
| 1063 | −10.2 | −6.9 | 18.9 | −15.2 | −22.6 | −27.8 |  |
| *1071 | −10.0 | 6.2 | 57.1 | 3.6 | −32.0 | −33.8 | −8.4 |
| *1077 | −8.6 | 0.8 | −15.0 | 25.8 | 17.5 | 32.3 | −3.4 |
| 1078 | −14.6 |  |  |  |  |  |  |
| 1080 | −5.0 | −5.1 | 14.3 | −11.4 | −19.1 | −22.6 |  |

TABLE 7

Effect of clarithromycin on weight, cholesterol levels, and triglyceride levels after six months of treatment.

| Patient # | Weight | Total Cholesterol | HDL | LDL | Total Cholesterol/HDL | LDL/HDL | Triglycerides |
|---|---|---|---|---|---|---|---|
| *1007 | −4.6 | 0.9 | 18.5 | 17.1 | −15.3 | −1.9 | −43.6 |
| *1029 | −5.8 | −18.2 | 158.8 |  | −68.6 |  | −64.0 |
| 1030 | −23.0 | −1.9 | 17.9 | −3.0 | −16.2 | −16.7 |  |
| 1034 | −12.1 | −3.5 | 27.8 | −1.3 | −19.0 | −17.9 |  |
| 1037 | −9.1 | −5.2 | 11.6 | −3.2 | −16.2 | −13.0 |  |
| *1042 | −10.5 | −7.4 | 29.0 | −28.6 | −28.8 | −24.4 | −45.5 |
| 1044 | −9.3 |  |  |  |  |  |  |
| 1063 | −10.2 | −2.2 | 16.7 | −10.1 | −16.1 | −22.2 |  |
| *1077 | −8.0 | −5.0 | −20.0 | 19.4 | 17.5 | 32.3 | −22.1 |
| *1080 |  | −5.0 | 2.6 | 16.7 | −0.7 | −12.8 | −12.9 |

TABLE 8

Effect of clarithromycin on weight, cholesterol levels, and triglyceride levels after seven months of treatment.

| Patient # | Weight | Total Cholesterol | HDL | LDL | Total Cholesterol/HDL | LDL/HDL | Triglycerides |
|---|---|---|---|---|---|---|---|
| 1018 | −5.3 | −17.2 | 13.7 | −26.7 | −26.8 | −34.5 | |
| 1030 | −25.1 | 9.7 | 53.6 | −3.0 | −29.7 | −37.5 | |
| 1034 | −11.0 | −4.0 | 7.4 | −6.4 | −0.5 | −14.3 | |
| *1042 | −8.6 | −9.3 | 22.6 | −3.1 | −25.8 | −19.5 | −49.8 |

TABLE 9

Effect of clarithromycin on weight, cholesterol levels, and triglyceride levels after eight months of treatment.

| Patient # | Weight | Total Cholesterol | HDL | LDL | Total Cholesterol/HDL | LDL/HDL | Triglycerides |
|---|---|---|---|---|---|---|---|
| 1030 | −26.5 | 10.1 | 8.9 | 17.2 | 0.0 | 8.3 | |
| 1034 | −10.0 | −2.6 | −7.4 | −0.7 | 4.8 | 7.1 | |
| *1042 | −8.3 | 5.9 | 61.3 | 14.8 | −34.8 | −29.3 | −58.2 |

Figure 1:
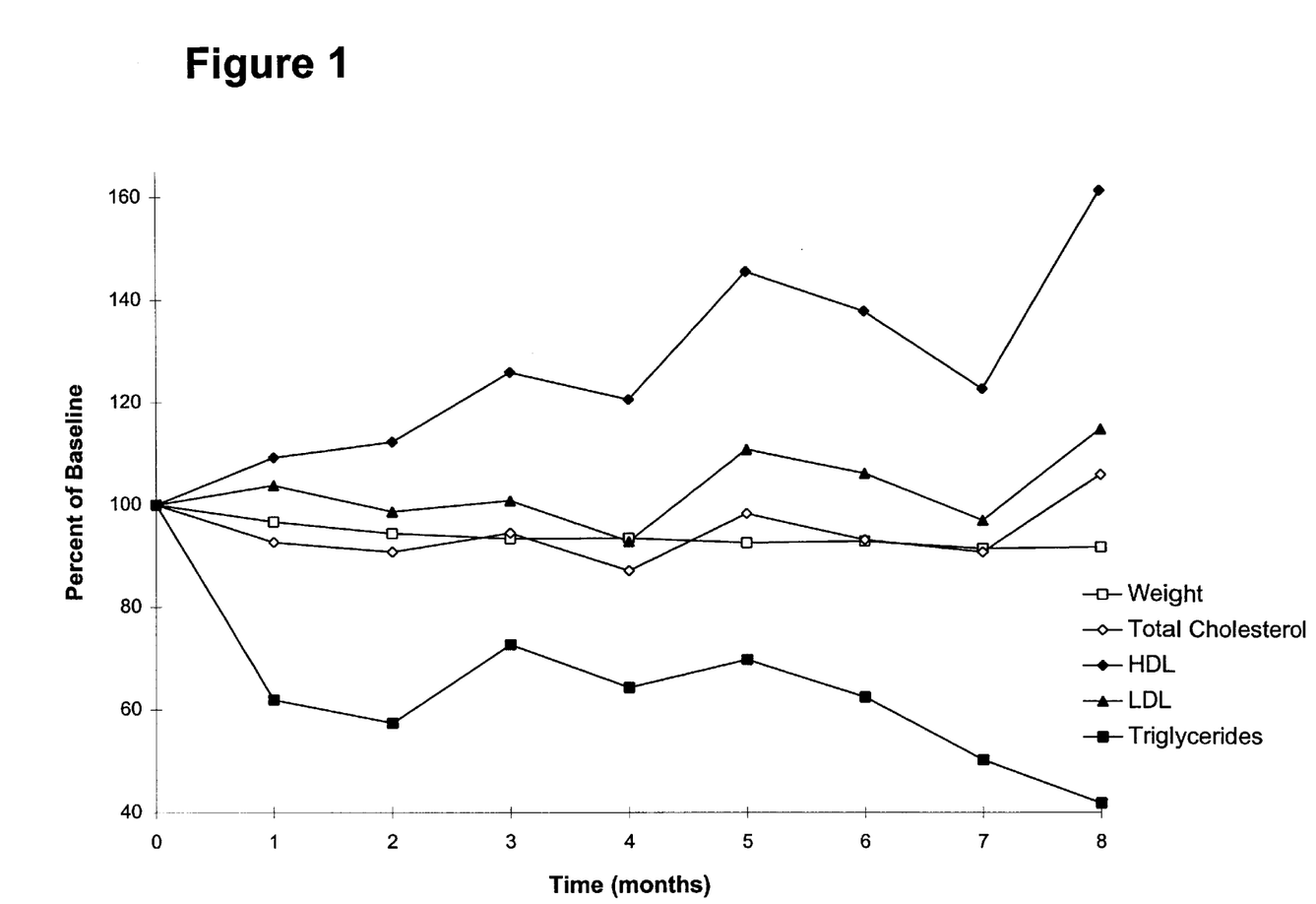
FIG. 1 depicts the effects of clarithromycin treatment on weight, total cholesterol levels, HDL cholesterol levels, LDL cholesterol levels, and triglyceride levels by plotting percent of baseline verses time in months. The presented data are measurements derived from patients diagnosed with hypertriglyceridemia. Baseline is the value measured before clarithromycin treatment and is set at 100% at time zero.
Figure 2:
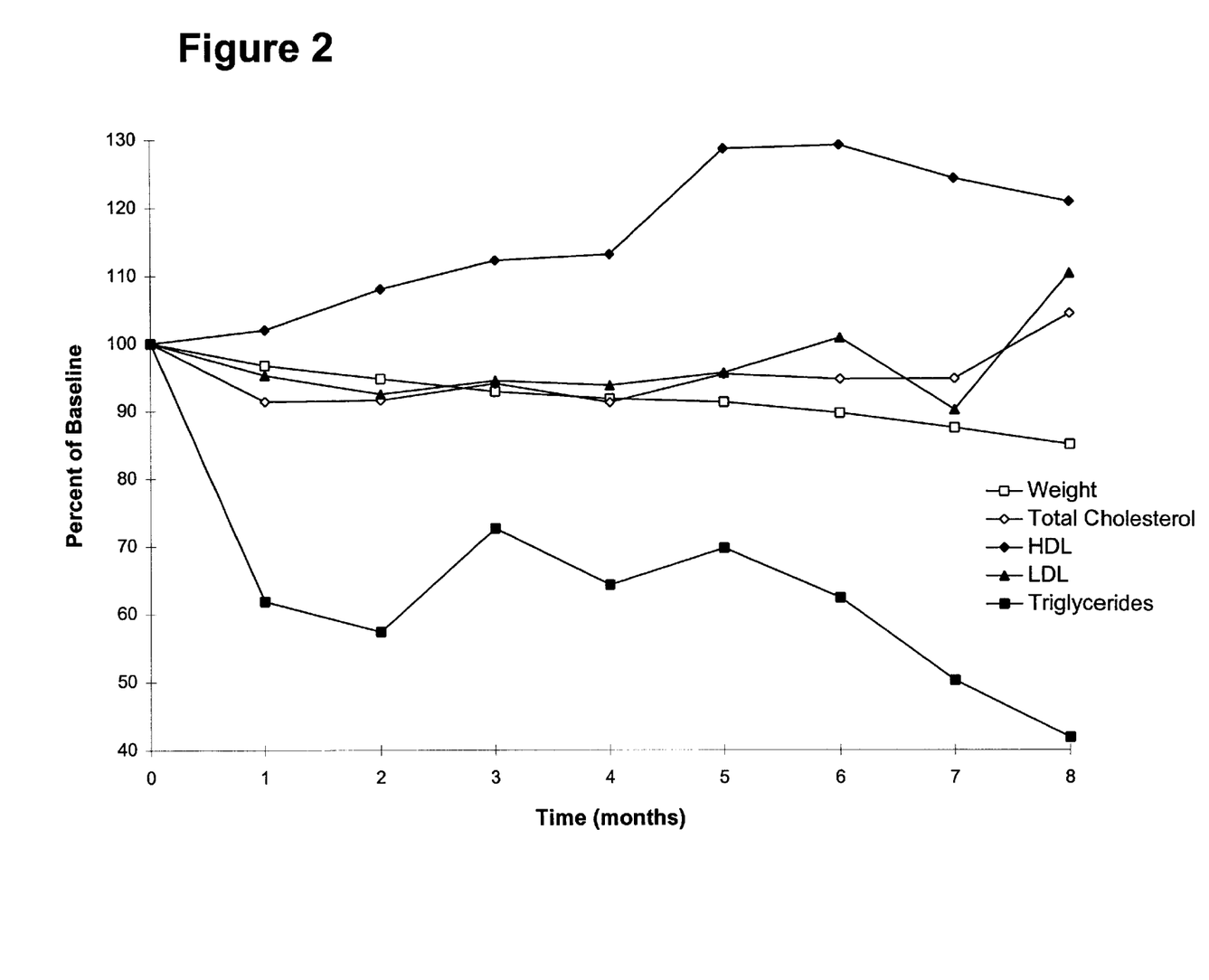
FIG. 2 depicts the effects of clarithromycin treatment on weight, total cholesterol levels, HDL cholesterol levels, LDL cholesterol levels, and triglyceride levels by plotting percent of baseline verses time in months. The presented data are measurements derived from patients receiving clarithromycin treatment for a variety of afflictions such as obesity, hypercholesterolemia, and hypertriglyceridemia. Baseline is the value measured before clarithromycin treatment and is set at 100% at time zero.

The average percent change for each month of clarithromycin treatment from patients diagnosed with hypertriglyceridemia is presented in Table 10. The number of patients (n) for each average is indicated. The averaged results for weight, cholesterol levels, and triglyceride levels are also presented as a chart plotting the percent of baseline verses time (FIG. 1). Baseline is the value measured before clarithromycin treatment. Therefore, the percent of baseline at time zero is 100% for each plasma component measured and changes thereafter. In addition, the average percent change (Table 11) and percent of baseline (FIG. 2) are presented for all patients receiving clarithromycin treatment. These patients were diagnosed with a variety of afflictions such as obesity, hypercholesterolemia, and hypertriglyceridemia.

TABLE 10

Effect of clarithromycin treatment on weight, cholesterol levels, and triglyceride levels from patients diagnosed with hypertriglyceridemia.

| Month | Weight (n) | Total Cholesterol (n) | HDL (n) | LDL (n) | Total Cholesterol/ HDL Ratio (n) | LDL/HDL Ratio (n) | Triglycerides (n) |
|---|---|---|---|---|---|---|---|
| 1 | −3.36 (18) | −7.39 (17) | 9.18 (17) | 3.77 (15) | −9.71 (17) | 1.27 (15) | −38.14 (18) |
| 2 | −5.68 (14) | −9.31 (14) | 12.21 (14) | −1.39 (12) | −11.49 (14) | −1.39 (12) | −42.64 (14) |
| 3 | −6.72 (10) | −5.60 (9) | 25.82 (9) | 0.73 (7) | −15.97 (9) | 5.11 (7) | −27.39 (10) |
| 4 | −6.60 (8) | −12.94 (8) | 20.51 (8) | −7.21 (7) | −18.66 (8) | −4.06 (7) | −35.74 (9) |
| 5 | −7.46 (5) | −1.78 (5) | 45.50 (5) | 10.80 (4) | −24.94 (5) | −10.68 (4) | −30.30 (5) |
| 6 | −7.23 (4) | −6.94 (5) | 37.78 (5) | 6.10 (4) | −19.18 (5) | −1.70 (4) | −37.62 (5) |
| 7 | −8.60 (1) | −9.30 (1) | 22.60 (1) | −3.10 (1) | −25.80 (1) | −19.50 (1) | −49.80 (1) |
| 8 | −8.30 (1) | 5.90 (1) | 61.30 (1) | 14.80 (1) | −34.80 (1) | −29.30 (1) | −58.20 (1) |

TABLE 11

Effect of clarithromycin treatment on weight, cholesterol levels, and triglyceride levels from all patients.

| Month | Weight (n) | Total Cholesterol (n) | HDL (n) | LDL (n) | Total Cholesterol/ HDL Ratio (n) | LDL/HDL Ratio (n) | Triglycerides (n) |
|---|---|---|---|---|---|---|---|
| 1 | −3.2 (68) | −8.6 (54) | 2.0 (54) | −4.7 (51) | −7.6 (54) | −2.6 (51) | −38.1 (18) |
| 2 | −5.2 (46) | −8.4 (38) | 8.0 (38) | −7.5 (33) | −11.1 (38) | −9.4 (33) | −42.6 (14) |
| 3 | −7.1 (35) | −6.0 (26) | 12.2 (26) | −5.5 (24) | −12.4 (26) | −10.5 (24) | −27.4 (10) |
| 4 | −8.2 (19) | −8.8 (17) | 13.1 (17) | −6.3 (16) | −14.5 (17) | −8.2 (16) | −35.7 (9) |
| 5 | −8.7 (11) | −4.5 (11) | 28.6 (11) | −4.4 (11) | −22.0 (11) | −18.7 (11) | −30.3 (11) |
| 6 | −10.3 (9) | −5.3 (9) | 29.2 (9) | 0.9 (8) | −18.2 (9) | −9.6 (8) | −37.6 (5) |
| 7 | −12.5 (4) | −5.2 (4) | 24.3 (4) | −9.8 (4) | −23.0 (4) | −26.5 (4) | −49.8 (1) |
| 8 | −14.9 (3) | 4.5 (3) | 20.9 (3) | 10.4 (3) | −10.0 (3) | −4.6 (3) | −58.2 (1) |

From this study it was concluded that clarithromycin is an affective medication for treating hypertriglyceridemia. Specifically, patients with elevated levels of plasma triglyceride levels responded positively to clarithromycin treatment in a relatively short period of time, usually with one month. Further, the percent reduction of triglyceride levels is quite dramatic, about 38% reduction within the first month of treatment. Moreover, these levels of reduction are approximately equal to the results obtained with other currently available hypolipidemic medications such as meucor 20 corpravachol.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing plasma triglyceride concentrations in a human comprising administering to said human an erythromycin compound at doses effective to reduce plasma triglyceride concentrations.

2. The method of claim 1, wherein said erythromycin compound is selected from the group consisting of clarithromycin, troleandomycin, erythromycin, and azithromycin.

3. The method of claim 2, wherein said compound is clarithromycin.

4. The method of claim 1, wherein said erythromycin compound is administered orally.

5. The method of claim 1, wherein said doses range from about 100 mg/day to about 6,000 mg/day.

6. The method of claim 1, wherein said doses range from about 1 mg/kg of body weight/day to about 100 mg/kg of body weight/day.

7. The method of claim 6, wherein said doses range from about 5 mg/kg of body weight/day to about 75 mg/kg of body weight/day.

8. The method of claim 7, wherein said doses range from about 10 mg/kg of body weight/day to about 25 mg/kg of body weight/day.

9. The method of claim 8, wherein said doses are about 11 mg/kg of body weight/day.

10. The method of claim 8, wherein said doses are about 22 mg/kg of body weight/day.

11. The method of claim 1, wherein said human has hypertriglyceridemia.

12. The method of claim 11, wherein said hypertriglyceridemia was diagnosed by a physician.

* * * * *